United States Patent

Simandan et al.

[11] Patent Number: 6,166,237
[45] Date of Patent: Dec. 26, 2000

[54] REMOVAL OF DISSOLVED SILICATES FROM ALCOHOL-SILICON DIRECT SYNTHESIS SOLVENTS

[75] Inventors: Tiberiu Ladislau Simandan; Frank D. Mendicino, both of Marietta, Ohio

[73] Assignee: Crompton Corporation, Greenwich, Conn.

[21] Appl. No.: 09/374,403

[22] Filed: Aug. 13, 1999

[51] Int. Cl.[7] .................................. C07F 7/18; C07F 7/04
[52] U.S. Cl. ........................ 556/470; 556/466; 568/635; 585/24; 585/25; 585/26
[58] Field of Search .................................. 556/470, 466; 568/635; 585/24, 25, 26

[56] References Cited

U.S. PATENT DOCUMENTS

| | | | |
|---|---|---|---|
| 2,486,992 | 11/1949 | Lewis et al. | 556/470 |
| 2,692,838 | 10/1954 | Thurber | 556/470 X |
| 3,627,807 | 12/1971 | Bieh | 556/470 |
| 3,641,077 | 2/1972 | Rochow | 556/470 X |
| 3,775,457 | 11/1973 | Muraoka et al. | 556/470 |
| 3,803,197 | 4/1974 | Anderson et al. | 556/470 |
| 4,113,761 | 9/1978 | Kreuzburg et al. | 556/470 |
| 4,288,604 | 9/1981 | Magee et al. | 556/470 |
| 4,323,690 | 4/1982 | Montle et al. | 556/470 |
| 4,762,939 | 8/1988 | Mendocino et al. | 556/470 |
| 5,166,384 | 11/1992 | Bailey et al. | 556/466 |
| 5,260,471 | 11/1993 | Yamada et al. | 556/470 |
| 5,362,897 | 11/1994 | Harada et al. | 556/470 |
| 5,441,718 | 8/1995 | Sharp | 423/338 |
| 5,527,937 | 6/1996 | Standke et al. | 556/470 |
| 5,728,858 | 3/1998 | Lewis et al. | 556/470 |
| 6,090,965 | 7/2000 | Lewis et al. | 556/470 |

*Primary Examiner*—Paul F. Shaver
*Attorney, Agent, or Firm*—Raymond D. Thompson

[57] ABSTRACT

Dissolved silanes, silicones and silicates from solvents used in the slurry phase Direct Synthesis of alkoxysilanes are removed by adding a compatabilizing agent and water to generate filterable precipitates and reusable solvent. The solvents are thereby remediated and made suitable for reuse in Direct Synthesis processes. Foaming is reduced with the remediated solvent and silicon conversion rates are higher. The precipitates are easily filtered and retain negligible quantities of solvent.

25 Claims, No Drawings

REMOVAL OF DISSOLVED SILICATES FROM ALCOHOL-SILICON DIRECT SYNTHESIS SOLVENTS

FIELD OF THE INVENTION

The present process relates to the removal of dissolved silanes, silicones and silicates from solvents used in the slurry phase Direct Synthesis of alkoxysilanes. The solvents are remediated thereby and made suitable for reuse in said Direct Synthesis. More particularly, the present invention discloses the use of a compatabilizing solvent and water to react with the dissolved silanes, silicones and silicates to generate readily filterable precipitates and reusable solvent.

BACKGROUND OF THE INVENTION

Trialkoxysilanes, especially trimethoxysilane and triethoxysilane, are used in the production of silane coupling agents. One method of synthesis of trialkoxysilanes is directly from silicon and an alcohol. This method is known variously in the art as the Direct Synthesis, the Direct Reaction, the Direct Process or the Rochow Reaction.

For trialkoxysilanes, Direct Synthesis is most conveniently performed in slurry reactors. In a slurry reactor for the Direct Synthesis of trialkoxysilanes, catalytically-activated silicon particles are maintained in suspension in an inert, high boiling solvent and are made to react with an alcohol at an elevated temperature. This type of reaction is disclosed in U.S. Pat. Nos. 3,641,077; 3,775,457; 4,727,173; 4,761,492; 4,762,939; 4,999,446; 5,084,590; 5,103,034; 5,362,897; 5,527,937, in co-pending U.S. application Ser. Nos. 08/728,228 and 08/729,266, and in Japanese Kokai Tokkyo Koho 55-28928 (1980), 55-28929 (1980), 55-76891 (1980), 57-108094 (1982) and 62-96433 (1987), 06-306083 (1994), all of which are incorporated herein by reference. Solvents disclosed in the aforementioned patents do not degrade under the activation and reaction conditions. Preferred examples are organic solvents with normal boiling points higher than about 250° C. that are stable at high temperature, and that are typically used as heat exchange media. Solvents meeting these criteria include the commercial products THERMINOL® 59, THERMINOL® 60, THERMINOL® 66, DOWTHERM® HT, MARLOTHERM® S, MARLOTHERM® L, as well as diphenyl ether, diphenyl, terphenyl, alkylated benzenes, alkylated diphenyls and alkylated terphenyls.

Tetraalkoxysilanes (also called alkyl silicates, esters of orthosilicic acid and silicon alkoxides) are prepared in slurry-phase Direct Synthesis processes wherein the solvent is often the product itself. The catalyst can be copper or a copper compound, but is usually an alkali or alkali metal salt of a high boiling alcohol. Such processes are disclosed in U.S. Pat. Nos. 3,627,807; 3,803,197; 4,113,761; 4,288,604 and 4,323,690, all incorporated herein by reference.

During the course of the Direct Synthesis of trialkoxysilanes, byproducts such as alkyl silicates accumulate in the solvent and contribute to an increase in viscosity, to a decline in catalytic activity and to foaming in the reaction slurry. These effects limit the long-term use of the solvent and necessitate its disposal or remediation. R. J. Ayen et al., "Better Ceramics Through Chemistry II," C. J. Brinker, D. E. Clark and D. R. Ulrich, Editors, Materials Research Society, Pittsburgh, Pa., 1986. pp 801–808, acknowledge this problem occurs with tetraethoxysilane manufacture, but they disclose no specific method of solvent or slurry disposal or recovery. U.S. Pat. No. 5,166,384 discloses the use of borates and alkali metal alkoxides to precipitate the contaminants and render the solvent reusable. Copending U.S. patent applicant Ser. No. 09/054,027 discloses the use of carboxylic acids in the remediation and reuse of the solvent.

All US patents and applications and all other published documents mentioned anywhere in this application are incorporated herein by reference in their entirety.

SUMMARY OF THE INVENTION

The present invention provides a method for the remediation and reuse of solvents from the Direct Synthesis of trialkoxysilanes and tetraalkoxysilanes. The method comprises the use of compatabilizing solvents and water in a hydrolysis reaction to yield a solid product from the dissolved silicates, siloxanes and silanes in the contaminated solvent. Thereafter, the remediated solvent is recovered for reuse in the Direct Synthesis process. Recovery may be accomplished by separation of the solvent from the solids material, and, if necessary, removal of excess compatabilizing agent and/or water from the separated solvent.

Filtration aids are optionally used prior to or after the compatabilizing solvents and water treatment to facilitate liquid/solid separation and improve the overall efficiency of the solvent remediation process.

The overall process is less wasteful of raw materials, more commercially viable and more environmentally acceptable than current commercial processes.

DETAILED DESCRIPTION OF THE INVENTION

Slurry-phase reactors for the Direct Synthesis of alkoxysilanes and tetraalkoxysilanes may be operated in a batchwise or continuous mode. In batchwise operation, a single addition of silicon and catalyst is made to the reactor at the outset and alcohol is added continuously, or intermittently, until the silicon is fully reacted, or reacted to a desired degree of conversion. The alcohol typically is added in the gas phase but liquid phase addition is also feasible. In continuous operation, silicon and catalyst are added to the reactor initially and thereafter to maintain the solids content of the slurry within desired limits. The batchwise mode is illustrated in U.S. Pat. Nos. 4,727,173, 5,783,720, and 5,728,858 all incorporated herein by reference. The desired reaction products are removed from the reactor in a gas phase mixture along with unreacted alcohol. Isolation of the product is accomplished readily by distillation according to known procedures.

Continuous Direct Synthesis of trialkoxysilanes is disclosed in U.S. Pat. No. 5,084,590 and of tetraalkoxysilanes in U.S. Pat. Nos. 3,627,807; 3,803,197 and 4,752,64, all incorporated herein by reference.

Silicon metal, catalyst and solvent can be added together in the reactor in any order. The solvent is present in an amount sufficient to disperse the solid and gaseous reactants homogeneously. Generally, reactions are initiated with solvent and solids in a gravimetric ratio between 1:2 and 4:1, preferably 1:1 to 2:1. However, as the silicon is consumed during batchwise Direct Synthesis, the solvent to solids ratio will increase. The ratio can be maintained within narrow limits of the preferred range for continuous reactions.

The desired reaction products are removed from the reactor in a gas phase mixture with alcohol reactant. Selection for trialkoxysilane or tetralkoxysilane can be accomplished by appropriate choice of catalyst and reaction conditions. Isolation of the desired trialkoxysilane and/or tetralkoxysilane from alcohol reactant is readily accomplished by distillation according to known procedures.

Owing to the disadvantages (for example, foaming, viscosity increase and loss of reaction efficiency) brought about by the accumulation of dissolved silicates and unreacted solids, the solvent must occasionally be treated for removal of these wastes. Otherwise, the performance of the Direct Synthesis deteriorates and the process becomes uneconomic.

Desirable products of the Direct Synthesis of trialkoxysilanes have the general formula, $HSi(OR)_3$, wherein R is an alkyl group of 1 to 6 carbon atoms. R is preferably methyl and ethyl. Byproducts of the synthesis comprise $Si(OR)_4$, $RSiH(OR)_2$, $RSi(OR)_3$, linear, branched and cyclic silicates such as $(RO)_3SiOSi(OR)_3$, $H(RO)_2SiOSi(OR)_2H$, $HSi(RO)_2OSi(OR)_3$, $(RO)_3SiOSi(OR)_2R$, $(RO)_3SiOSi(RO)_2OSi(RO)_3$, $(RO)_3SiOSi(OR)HOSi(OR)_3$, $(RO)_3SiOSi(OR)(R)OSi(OR)_3$, $(RO)Si[OSi(OR)_3]_3$, $(RO)_3SiOSi(OR)(OSi(OR)_3)OSi(OR)_3$, and $[OSi(OR)_2]_n$, (n=4, 5, 6 . . . ), hydrogen gas, hydrocarbons (RH) such as methane and ethane, alkenes ($R'CH=CH_2$) such as ethylene and ethers (ROR) such as dimethyl ether and diethyl ether. In the general formula, $R'CH=CH_2$, for the alkene byproducts, R' is hydrogen or an alkyl group of 1 to 4 carbon atoms. Hydrogen gas, hydrocarbons and the ethers typically are not condensed in the cold trap with the liquid products and exit the apparatus as a gaseous stream. Some of the silicates are volatilized out of the reactor and are soluble in the liquid reaction product. Most remain solubilized in the solvent or precipitate as insoluble gels.

Descriptions of the silicon and copper raw materials used in the Direct Synthesis of trialkoxysilanes are provided in U.S. Pat. Nos. 3,775,457 and 4,727,173, and in U.S. Pat. Nos. 5,783,720 and 5,728,858 all incorporated herein by reference. Used solvent also contains dark colored particles, which are derived from the silicon and copper or alkali metal catalyst charged to the reactor. The particles may contain silicon, copper, iron, aluminum, chromium, manganese, nickel, oxygen, phosphorus and titanium among other elements, and sometimes are difficult to separate by filtration or centrifugation, especially if gelatinous silicates are also present. Primary particles range in size from submicrometer to about 50 micrometers. Agglomerates are considerably larger.

Solid and/or liquid filtration aids optionally are added to facilitate separation of these solids prior to or subsequent to the addition of the compatabilizing solvent and water. Suitable filtration aids include cellulose-based products such as SOLKAFLOC®; acrylates such as GOOD-RITE® 7058, CARBOPOL® 980, PEMULEN® TR1, PEMULEN® TR2, and PEMULEN® 1622; MILLITHIX® 925; polyethylene oxide, polypropylene oxide and their copolymers; diatomaceous filter aids such as CELITE® and CELATOM® products; and inorganic silicates like calcium silicate and magnesium silicate. Mixtures of these filter aids may also be employed advantageously. The quantity of filter aid required for effective solids collection depends, among other factors, on the particle size and surface properties of the filter aid, on the solids content of the used reaction solvent and whether they are gelatinous or crystalline. As little as 0.1 weight percent (based on total weight of used solvent) might be sufficient in some cases, whereas in others an amount of filter aid equal to the weight of the contained solids might be necessary for fast, uninterrupted filtration and clarification. In cases where the solids are primarily gelatinous, still higher amounts of filter aid may be necessary. Additionally, it is often found experimentally that some materials exhibit an optimum use level beyond which the excess filtration aid might slow the rate of filtration. Thus, all cellulosic, siliceous, acrylate and polymeric filter aids are not all equally effective. Preferred materials for the process of this invention are SOLKAFLOC®, PEMULEN® TR1, PEMULEN® TR2, PEMULEN® 1622, GOOD-RITE® 7058 and CARBOPOL® 980.

It is preferable to remove the suspended solids prior to the purification. However, this step is not absolutely required. Separation of solids from the used solvent with the aid of effective amounts of filter aid is desirable if the solvent is recycled to the Direct Synthesis without precipitation of dissolved silicates.

Slurry for disposal from the Direct Synthesis of tetraalkoxysilanes is similar to that just described, but has considerably less copper and more alkali metal salts (for example, sodium ethoxide, sodium methoxide or sodium 2-ethoxyethylate). These salts make the slurry very alkaline.

Solvents useful in the Direct Synthesis of alkoxysilanes are thermally stable and do not degrade under the activation and reaction conditions of the synthesis. The preferred solvents for trialkoxysilanes are high temperature stable organic solvents typically used as heat exchange media. Examples include THERMINOL® 59, THERMINOL® 60, THERMINOL® 66, DOWTHERM® HT, MARLOTHERM® S, MARLOTHERM® L, diphenyl ether, diphenyl, terphenyl and alkylated benzenes, alkylated diphenyls and alkylated terphenyls with normal boiling points higher than about 250° C.

THERMINOL® is the Monsanto Company trade name for heat transfer fluids. THERMINOL® 59 is a mixture of alkyl-substituted aromatic compounds recommended for use between −45 to 315° C. THERMINOL® 60 is a mixture of polyaromatic compounds with an average molecular weight of 250. Its optimum temperature range is from −45° to 315° C. THERMINOL® 66 and DOWTHERM® HT are mixtures of hydrogenated terphenyls with an average molecular weight of 240. Maximum temperature limit is about 370° C. THERMINOL® 59, THERMINOL® 66 and DOWTHERM® HT are preferred solvents of this invention. DOWTHERM® fluids are produced by Dow Chemical Company.

MARLOTHERM® is the Hüls AG trade name for its heat transfer fluids. MARLOTHERM® S is a mixture of isomeric dibenzylbenzenes. MARLOTHERM® L is a mixture of isomeric benzyl toluenes. Both can be used at temperatures up to about 350° C. Both are preferred solvents for the instant invention.

Suitable alkylated benzenes are dodecylbenzene, tridecylbenzene, tetradecylbenzene and their mixtures such as are sold by Vista Chemical Company under the trade name NALKYLENE®. NALKYLENE® 550BL, NALKYLENE® 550L and NALKYLENE® 600L are particularly preferred solvents of this invention. Mixtures of alkylated benzenes and polyaromatic hydrocarbons are also useful solvents for the Direct Synthesis of alkoxysilanes.

The Direct Synthesis of tetraalkoxysilanes preferably is conducted with the product as solvent. However, aromatic solvents such as dibenzyltoluenes and diisopropylbenzene, and/or ether solvents such as triethyleneglycol dimethyl ether may be admixed with the tetraalkoxysilane. Useful solvents are identified in U.S. Pat. Nos. 3,803,197; 4,113,761 and 4,752,647, applicable portions of which are incorporated herein by reference.

Gravimetry and atomic absorption spectroscopy are suitable methods for quantifying the total silicon content of the used reaction solvent. Analytical procedures are published, for example, in "The Analytical Chemistry of Silicones," (A. L. Smith, Editor), John Wiley & Sons Inc., N.Y., 1991, chapter 8. Soluble silicates can be analyzed qualitatively and quantitatively by infrared spectroscopy. Si—O—Si bonds are indicated by strong absorption in the 1000–1200 cm$^{-1}$ range. $^{29}$Si nuclear magnetic resonance (NMR) spectroscopy can be used to detect and quantify the different silicon-containing species in the used solvent.

The instant method of waste treatment and reuse of solvent is applicable to any solvent or mixture of solvents employed in the Direct Synthesis of alkoxysilanes and tetraalkoxysilanes. The method comprises addition of a compatabilizing agent and water to the used solvent, separation of the solid and volatile reaction products and recovery of the remediated solvent for reuse. In order to facilitate safe disposal of the solid waste, it is desirable to produce a granular solid, which settles or filters readily and which has little or no capacity to retain the reaction solvent.

Suitable compatiblizing solvents are ones which allow the water present in the reaction solvent which is normally a separate phase to be at least partially miscible with the reaction solvent so that the concentration of water exceeds the solubility of water in the solvent without the compatibilizing agent, preferably by at least a factor of ten, more preferably by a factor of at least 100. More preferably the compatabilizing solvent will allow the water to be infinitely miscible in the reaction solvent. This allows the water to react with the side products present in the used solvent.

Partial miscibility may be determined by shaking together one milliliter portions of each solvent comprising a pair for approximately a minute at 20° C. If no interfacial meniscus is observed after the contents of the tube are allowed to settle, the solvent pair is considered to be miscible. If a meniscus is observed without apparent change in the volume of either solvent, the pair is regarded as immiscible. Although this classification is a qualitative one since solvent pairs may exhibit various degrees of partial miscibility while existing as separate phases, if an obvious change occurs in the volume of each solvent but a meniscus is present, the pair is classified as partially miscible.

Examples of compatiblizing solvents include alcohols, preferably $C_1$–$C_4$ such as methanol, ethanol and isopropanol, mono and polyglycol ethers, e.g. ethylene glycol dimethyl ether and higher oligomers thereof, ketones $C_4$ or less such as acetone and methylethylketone and ethers such as tetrahydrofuran and dioxane and combinations of the above. A condensation catalyst such as a metal alkoxide, for example, titanium isopropoxide, aluminates, and sodium alkoxides may be used in conjunction with the compatabilizing agent. The compatabilizing agent will preferably have a boiling point less than that of the used solvent to allow for stripping of excess compatabilizing agent from the used solvent. The compatabilizing agent must be added separately from water-preferably after water addition.

Desirably, the compatabilizing agent is added to the used solvent in an amount which provides a ratio of compatabilizing agent to used solvent from about 1:20 to about 1:1 by weight. More desirably, the ratio of compatabilizing agent to used solvent is from about 1:10 to about 1:4 by weight. Even more desirably, the ratio of compatabilizing agent to used solvent is about 1:4 by weight.

All of the compatabilizing agent(s) may be added to the used solvent at one time. The compatabilizing agent(s) may also be added over time. Where one or more compatabilizing agent is added over time, later additions may be made at elevated temperatures relative to the initial addition of compatabilizing agent.

Desirably, water is added to the used solvent in an amount which provides a ratio of water to dissolved silicates in the used solvents from about 1:2 to about 10:1 by molar ratio of $H_2O$ to contained Si. More desirably, water is added to the used solvent in an amount which provides a ratio of water to dissolved silicates from about 1:2 to about 2:1 by molar ratio of $H_2O$ to contained Si.

Once the water is miscible with the solvent, the alkoxysilanes can react with water to produce condensed silicates. Further condensation of the reaction products can lead to gels and solids. Used Direct Synthesis solvents which contain alkoxy silanes are water reactive, even with atmospheric moisture.

The SiOR and SiOH functionalities are present in dissolved or suspended silicates, silanes and siloxanes in the used solvent. SiOSi formation eventually leads to precipitation of solid silicates and silica. The corresponding alcohols are the volatile byproducts. It can be incinerated or used beneficially, if desired. For example, the alcohol can be used to wash excess acid and solvent from the precipitated solid prior to landfilling.

The quantity of compatabilizing agent added to the waste solvent must be sufficient to solubilize the added water in the used solvent.

In the event that an excess of compatabilizing agent and/or $H_2O$ is used, it can be removed from the treated solvent by evaporation, by adsorption on a suitable solid such as activated carbon or by chemical conversion to a volatile ester or insoluble salt. Evaporation can be effected at normal or reduced pressures, and with the aid of heat and an inert gas flow.

Temperatures in the range, 15–150° C., preferably 20–100° C., may be used for safe and effective treatment of the used solvent. Selection of the most suitable temperature is determined by, among other factors, volatility of the ester and alcohol, exothermicity of the hydrolysis, ease of filtration of the solids formed and configuration of the available equipment. For acetone, for example, the hydrolysis may be carried out at a temperature of about 56° C. while for isopropyl alcohol, the hydrolysis may be carried out at a temperature of about 82° C.

The time of the hydrolysis reaction can be from about ten minutes to about six hours or longer. Reaction times from about thirty minutes to about three hours are preferred for the process of the instant invention.

The reaction may be run under acidic conditions. To that end, boric acid desirably in an amount from about 0.1% to 10% by weight of the water added or other suitable acids may be added in addition to the compatabilizing agent. Desirably, the reaction will be run at a pH of about 7±1.

A process for the removal of dissolved silicates, silanes and siloxanes from the used solvents with compatabilizing agent and $H_2O$ can be accomplished in a number of ways. In some cases, it might be advantageous to perform the hydrolysis treatment, prior to separation of the silicon and catalyst solids, in the same reactor used for the Direct Synthesis. Thus, after one or more batches of silicon has been reacted with an alcohol and there is a need to remediate and recycle the solvent, the alcohol feed to the reactor is terminated and the compatabilizing agent and $H_2O$ is added to the stirred reaction slurry at a temperature that is above the normal boiling point of the alcohol. The volatile byproduct (alcohol) is taken overhead and optionally incinerated. Compatabilizing agent and $H_2O$ is added at a rate and in an amount sufficient to remove the dissolved silicates, siloxanes and silanes. The slurry comprising silicon, catalyst (that is, containing copper, alkali metal or alkaline earth metal) solids, the precipitated silicates and solvent with minor amounts of alcohol, optionally acid and compatabilizing agent is discharged from the reactor into a filter, centrifuge or other liquid/solid separator. Filtration aids optionally are added to increase the ease and speed of the separation. The solids optionally are washed with the alcohol and landfilled or otherwise safely discarded. Recovered solvent is recycled to the Direct Synthesis reactor. All volatiles, which include compatabilizing agent, are stripped from the solvent as it is being reheated to resume the Direct Synthesis. Silicon and catalyst are added to the hot, stripped solvent with appropriate safety and caution at a temperature below the initiation temperature of the Direct Synthesis.

Alternatively, the hot slurry from the Direct Synthesis optionally is treated with an effective amount of a filtration aid and discharged directly into a solid/liquid separator (for example, centrifuge or filter) for removal of the waste solids. The filtrate, which can still contain ultrafine particulates, is admitted into a separate vessel, or optionally the original reactor, where it is agitated, treated with the compatabilizing solvent and water and maintained at a temperature sufficient to volatilize the byproduct alcohol. The compatabilizing agent and $H_2O$ is added at a rate and in an amount sufficient to effect removal of silanes, silicates and siloxanes. Solids are separated from the remediated solvent, optionally with the assistance of filtration aids, by centrifugation or filtration. The solvent is recycled to the Direct Synthesis.

The following Examples illustrate the preferred embodiments of the instant invention. These are not intended to limit the scope of the invention. Rather, they are presented merely to facilitate the practice of the invention by those of ordinary skill in the art.

EXAMPLES

Abbreviations used in the presentation of the data of the illustrative examples are the following:

TABLE 1

| ABBREVIATION | MEANING | ABBREVIATION | MEANING |
|---|---|---|---|
| kPa | kilopascals | g | gram |
| psig | pounds per square inch gauge | kg | kilogram |
| Selectivity | $HSi(OR)_3/Si(OR)_4$ | L | liters |
| N550BL | NALKYLENE ® 550BL | µm | micrometer |
| TH 59 | THERMINOL ® 59 | % Si/hr converted per hour | percent silicon |
| sec | second | rpm | revolutions per minute |
| min | minute | m²/g | square meters per gram |
| hr | hour | wt % | weight percent |
| | | cm | centimeter |

In Example 1, used solvent was analyzed by gravimetry and atomic absorption spectrometry for total silicon content and by $^{29}Si$ NMR for the speciation of the soluble silicon into $Q^0$, $Q^1$, $Q^2$, $Q^3$ and $Q^4$ groups. The chemical shifts (relative to tetramethylsilane) of these functional groups are set forth in Table 2, below. Molar percentages of these groups are calculated from the integration areas.

TABLE 2

| GROUP | STRUCTURE | $^{29}Si$ NMR SHIFTS (ppm) |
|---|---|---|
| $Q^0$ | $\underline{Si}(OR)_4$ | −78.3 to −78.5 |
| $Q^1$ | O-$\underline{Si}(OR)_3$ | −85.6 to −85.9 |
| $Q^2$ | O-$\underline{Si}(OR)_2$-O | −93.6 to −93.9 |
| $Q^3$ | O-$\underline{Si}$-O(OR)O | −102.0 to −102.6 |
| $Q^4$ | $\underline{Si}(OSi)_4$ | −110 |

Preparation of Synthetic Silicate Mixture

Following the procedure published by W. G. Klemperer and S. D. Ramamurthi in "Better Ceramics Through Chemistry III," (Brinkley, Clark and Ulrich, Editors), p.3, a mixture of linear, branched and cyclic silicates was prepared from 112.09 g $CH_3OH$, 22.42 g $HSi(OCH_3)_3$, 86.24 g $Si(OCH_3)_4$, 7.14 g $H_2O$ and 1.45 g 10 molar HCl. This mixture was used in comparative experiments reported in Example 1 to illustrate the spectroscopic properties of alkyl silicates.

Example 1

This Example illustrates the content of silicon, dissolved silicate and total solids of waste solvents from laboratory and industrial slurry phase Direct Syntheses of trimethoxysilane.

TABLE 3

Silicon And Silicate Composition of Used Reaction Solvents And Synthetic Silicate Waste

| SAMPLE | wt % Si in SOLVENT | $Q^0$, mole % | $Q^1$, mole % | $Q^2$, mole % | $Q^3$, mole % |
|---|---|---|---|---|---|
| Used TH 59 Laboratory | 0.34 | 0 | 52.3 | 47.7 | 0 |
| Used TH 59 Industrial | 1.85 | 7.9 | 15.5 | 30.6 | 29.5 |
| Used N550 | 0.87 | 0 | 44.2 | 39.8 | 13.8 |
| Synthetic silicate mixture | 9.17 | 13.3 | 34.9 | 35.0 | 12.6 |

Example 2

This Example illustrates the improvements in solid/liquid separation rate effected by the addition of filter aids to the used reaction solvent. Several polyacrylate (GOOD-RITE® 7058, CARBOPOL® 980, PEMULEN®, cellulose-based (SOLKAFLOC®), sorbitol-based (MILLITHIX® 925) and polyethylene oxide filtration aids were tested. The data shown in Table 3 are for 0.5 wt % use level in used THERMINOL® 59 from the commercial scale Direct Synthesis of $HSi(OCH_3)_3$ In each experiment, 200 g of the used solvent were stirred at 21° C. with the appropriate filter aid. Filtration was performed through 142 mm diameter, 0.7 micrometer borosilicate microfiber pads in a stainless steel filter pressurized at 20 psig 137.9 kPa) nitrogen. Filtrate was weighed intermittently during collection and a plot of weight versus time was constructed. The rate (g/min) shown in Table 4 is the slope of the linear, rising portion of the curve. Approximately 190 g was recovered from each experiment.

TABLE 4

Filtration of Used Therminol ® 59 with Filtration Aids.

| FILTER AID | WEIGHT OF FILTRATE, g | TOTAL TIME, min | FILTRATION RATE, g/min |
|---|---|---|---|
| None | 192.0 | 15.5 | 22.31 |
| GOOD-RITE ® 7058 | 189.4 | 4.67 | 130.95 |
| CARBOPOL ® 980 | 189.5 | 9.67 | 43.64 |
| MILLITHIX ® 925 | 191.7 | 10.83 | 26.22 |
| POLYOX 7 × $10^6$ daltons | 191.8 | 9.50 | 34.53 |
| PEMULEN ® TR1 | 192.0 | 8.00 | 48.94 |
| PEMULEN ® TR2 | 192.0 | 8.50 | 48.92 |
| PEMULEN ® 1622 | 191.0 | 8.17 | 48.84 |
| SOLKAFLOC ® | 192.0 | 4.67 | 121.43 |

The data of Table 4 show that filtration was enhanced to different extents with the addition of 0.5 wt % filter aid. Polyacrylate and cellulose-based materials afforded rate improvements 2–6 times the control value. GOOD-RITES® 7058 and SOLKAFLOC® were especially effective.

General Reaction Procedure (Examples 3–17)

The silicate-containing alkyl-substituted aromatic solvent ("Solvent A") used in examples 3–17 was a dark gray, very viscous liquid (200 centistoke), having about 12.3% silicon (as siloxanes, silanes, etc.). It had an initial content of 28% solids and 72% liquid (determined by a 2-day long pressure filtration).

In most of the cases, 150.0 g methanol and 30.0 g water were added at room temperature to 600.0 g unfiltered, silicate-containing Solvent A which had been used in the Direct Reaction of several batches of silicon with methanol. The mixture was stirred and heated to reflux for 3 hours, then stripped by heating at 120° C. with a slight nitrogen sparge. The solids formed were filtered out after cooling to below 60° C. The recovered filtrate contained typically 50 to 200 ppm silicon compounds, determined by AAS. In another variation, after the mixture was stirred and heated for 3 hours at 60° C. the solids were filtered using a pressure filter with filter paper, and the filtrate was returned to the flask and stripped at 120° C. using a slight nitrogen sparge.

Example 3

In a 4 liter round bottomed flask with 4 necks, 600.25 g of spent Solvent A, 150.49 g methanol and 30.33 g of water were mixed together at room temperature. The flask was equipped with a distillation head, thermometer, addition funnel and a mechanical stirrer. The spent Therminol had the characteristics described in the general reaction procedure. The mixture was heated to reflux for 3 hours. The excess water and methanol were then stripped off by gradually heating to 120° C. and applying a slight nitrogen sparge. About 188 g lights were collected. The flask was cooled to 70° C. and the content was transferred to a pressure filter utilizing a #4 filter paper. The filtrate, in an amount of 381.7 g, was a golden clear liquid. It was analyzed and determined to have a silicon content of 421 ppm. The solid, in an amount of 189.5 g, was a wet, clumpy and grainy, dark gray material. The filtration was easy and fast, followed by nitrogen blow down for 5 minutes. During the strip, foaming occurs, which dissipates at higher temperature.

Example 4

In the same experimental setup, 601.2 g of spent Solvent A were mixed with 135.1 g methanol, 15.3 g ethanol and 31.2 g water. The reaction was run in the same conditions as above in Example 3. The stripping step yielded 190.8 g lights. The solid (169.0 g) was a dark gray and grainy material. About 431.6 g Solvent A solvent was recovered with a 638 ppm silicon content. Some foaming occurred during the strip.

Example 5

The reaction was run as in Example 3, except that methanol was replaced with 150.0 g acetone. At the end, 183.3 g lights, 306.1 g solids and 275.7 g Solvent A with 2614 ppm Si content, were collected. The filtration was slower and the solid looked wet and very finely divided.

Example 6

The reaction was run as described in Example 3 except that methanol was replaced with 153.3 g tetrahydrofuran (THF). About 174.3 g lights, 231.4 g solids and 166.3 g Solvent A with 209 ppm Si, were collected. No foaming occurred during the strip.

Example 7

The reaction was run as described in Example 4 except that the ethanol/water mixture was added later, at 55° C. About 181.0 g lights, 164.0 g solids and 21.2 g Solvent A with 1688 ppm Si, were collected. Foaming occurred during the strip. The solid was grainy and wet.

Example 8

The reaction was run as described in Example 3 except that the methanol as replaced with 150.7 g iso-propanol (IPA). The reaction yielded 183.0 g lights, 243.6 solids and 344.8 g Solvent A having 169 ppm silicon. No foaming occurred during the trip. The solid was finer and sandy.

Example 9

The reaction was run as described in Example 3 except that, instead of pure methanol, a 135.2 g methanol with 16.0 g IPA mixture was used. About 188.2 g lights, 195.5 g solids and 388.9 g Solvent A having 141 ppm Si, were recovered. Slight foaming occurred during the strip. The solid was grainy and easy to filter.

Example 10

The reaction was run as described in Example 9 except that methanol was added at room temperature while IPA and water mixture were added at 52° C. At the end, 187.8 g lights, 159.0 g solids and 427.9 g Solvent A having 603 ppm Si, were recovered. Light foaming occurred during the strip. The solid was dark gray with large particle size.

Example 11

The reaction was run as described in Example 10 except that 10.0 g of boric acid was added to the initial reaction mixture. About 199.4 g lights, 150.4 g solids and 434.0 g Solvent A having 66 ppm Si, were collected. Light foaming occurred during the strip. The solid was dark gray, with large particle size.

Example 12

Using the experimental set-up described in Example 3, 600.6 g spent Solvent A, 150.7 g methanol and 31.8 g water were added together at room temperature. The reaction mixture was stirred at 60° C. for 3 hours. At this time, the solids formed were filtered off in the pressure filtration unit. The liquid filtrate was returned to the flask and stripped by heating to 120° C. and applying a light nitrogen sparge. No foaming occurred during this strip. The solids (272.3 g) were dark gray with large size particles and very easy to filter. The reaction yielded 6.0 g lights and 443.2 g Therminol having 3218 ppm Si content.

Example 13

The reaction was run in the conditions described in Example 12 except that methanol and water mixture was added at 54° C. No foaming occurred during the strip and the solids (278.5 g) were similar with the ones in Example 12. Also, 7.4 g lights and 445.3 g of Solvent A having 2980 ppm Si, were collected.

Example 14

The reaction was run in the conditions described in Example 9 except that solvent A was mixed with IPA, methanol and 20.2 g water having pH=4 by addition of 10.1 g buffer solution (potassium hydrogen phthalate). The reaction yielded 190.8 g solids, 188.3 g lights and 391.9 g Solvent A having 90 ppm Si content.

Example 15

The reaction was run as in example 7 except that, at 64° C., after 1 hour, 10.1 g titanium isopropoxide ware added to the mixture. The reaction produced 238.0 g solids, 190.6 g lights and 337.7 g Solvent A with 27 ppm Si content.

Example 16

The reaction was run as described in Example 10 except that spent Solvent A was replaced with uncentrifuged spent Solvent A containing unreacted silicon metal and copper catalyst. The reaction occurred and yielded similar quality and quantity materials as in Example 10.

In addition to being directed to the specific combinations of features claimed below, the invention is also directed to embodiments having other combinations of the dependent features claimed below and the features described above. To that end, all possible alternative dependent combinations of the features recited in the dependent claims, whether written in multiple dependent form or not, should be considered to be within the scope of the invention.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A process for remediating a used solvent containing dissolved silicon compounds therein, the process comprising:
   contacting the used solvent with a sufficient amount of a compatabilizing agent and water, the compatabilizing agent chosen so as to render the water at least partially miscible in the used solvent, so as to effect a reaction which converts said dissolved silicon compounds to solid silicates and/or silica; and then,
   separating the solvent from the solid silicates and/or silica.

2. A process as in claim 1 wherein, prior to said contacting step the solvent is separated from solids suspended therein.

3. A process as in claim 2 wherein the compatabilizing agent is added to the used solvent in an amount which provides a ratio of compatabilizing agent to used solvent from about 1:20 to about 1:1 by weight.

4. A process as in claim 3 wherein the ratio of compatabilizing agent to used solvent is from about 1:10 to about 1:4 by weight.

5. A process as in claim 1 wherein an excess of water is used and, after said solid silicates and/or silica are produced, excess water is stripped from the solvent.

6. A process as in claim 1 wherein the compatabilizing agent is selected from the group consisting of alcohols, ketones, ethers and combinations thereof.

7. A process as in claim 1 wherein the compatabilizing agent is selected from the group consisting of methanol, ethanol, isopropanol and combinations thereof.

8. A process as in claim 1 wherein the compatabilizing agent is ethylene glycol alkyl ethers and higher oligomers.

9. A process as in claim 1 wherein the compatabilizing agent is selected from the group consisting of acetone, methylethylketone and combinations thereof.

10. A process as in claim 1 wherein the compatabilizing agent is selected from the group consisting of tetrahydrofuran, dioxane and combinations thereof.

11. A process as in claim 1 wherein said reaction is effected at a temperature of 15–150° C.

12. A process as in claim 1 wherein after contacting the used solvent with the compatabilizing agent and water, the used solvent with the compatabilizing agent and water is heated to reflux.

13. A process as in claim 1 wherein the used solvent has a boiling point of greater than 250° C.

14. A process as in claim 13 wherein the used solvent is an alkylated aromatic compound, a polyaromatic compound, triethyleneglycol dialkyl ether or a mixture of two or more thereof.

15. A process as in claim 13 wherein the used solvent comprises at least one member selected from the group consisting of diphenyl ether, diphenyl, terphenyl, alkylated benzenes, alkylated diphenyls, alkylated terphenyls, dibenzyl benzenes, benzyl toluenes, hydrogenated terphenyls and triethyleneglycol dialkyl ether.

16. A process as in claim 1 further comprising adding a filtration aid prior to or subsequent to contacting the used solvent with the water and compatabilizing agent.

17. A process as in claim 16 wherein said filtration aid is a member of the group consisting of cellulosic, acrylic, polyethylene oxide, polypropylene oxide, poly(ethylene oxide/propylene oxide) copolymers, diatomaceous and inorganic silicate filter aids, and mixtures thereof.

18. A process as in claim 1 wherein the solvent is a used solvent from a Direct Synthesis process for production of an alkoxysilane.

19. A process as in claim 18 wherein the alkoxysilane is a trialkoxysilane or a tetraalkoxysilane.

20. A process as in claim 1 wherein the water is added to the used solvent in an amount which provides a ratio of water to dissolved silicates in the used solvents from about 1:2 to about 10:1 by molar ratio of $H_2O$ to contained Si.

21. A process as in claim 1 wherein the water is added to the used solvent in an amount which provides a ratio of water to dissolved silicates in the used solvents from about 1:2 to about 2:1 molar ratio of $H_2O$ to contained Si.

22. A process as in claim 1 wherein boric acid is added to the used solvent.

23. A process as in claim 1 wherein the used solvent is further contacted by a metal alkoxide.

24. A process as in claim 23 wherein the metal alkoxide is titanium isopropoxide.

25. A process comprising:
 a) reacting a mixture of silicon and alcohol in a reaction solvent under conditions which produce an alkoxysilane product;
 b) separating the alkoxysilane product from the reaction mixture; and then,
 c) remediating the used solvent by
  i) contacting the used solvent with a sufficient amount of a compatabilizing agent and water so as to effect a reaction which converts dissolved silicon compounds in the used solvents to solid silicates and/or silica; and then,
  ii) separating the solvent from the solid silicates and/or silica.

* * * * *